United States Patent [19]

Newhouse et al.

[11] Patent Number: 5,349,947
[45] Date of Patent: Sep. 27, 1994

[54] DRY POWDER INHALER AND PROCESS THAT EXPLOSIVELY DISCHARGES A DOSE OF POWDER AND GAS FROM A SOFT PLASTIC PILLOW

[76] Inventors: Michael T. Newhouse, 436 Queen Street South, Hamilton, Ontario, Canada, L8N 4A6; W. Douglas Baines, 1675 Wedmore Way, Mississauga, Ontario, Canada

[21] Appl. No.: 92,085

[22] Filed: Jul. 15, 1993

[51] Int. Cl.$^5$ ............... A61M 15/00; A61M 16/00; A61M 13/00; B65D 83/04
[52] U.S. Cl. ............... 128/203.21; 128/203.15; 604/58; 206/531
[58] Field of Search ............... 128/203.15, 203.12, 128/203.21, 200.21, 200.22; 604/58-64, 77; 206/531-533, 538, 539

[56] References Cited

U.S. PATENT DOCUMENTS

| | | | |
|---|---|---|---|
| 2,549,303 | 4/1951 | Friden | 128/203.15 |
| 3,367,535 | 2/1968 | Tanguay | 128/203.15 |
| 4,905,866 | 3/1990 | Bartell et al. | 128/203.15 |

FOREIGN PATENT DOCUMENTS

| | | | |
|---|---|---|---|
| 0469814 | 2/1992 | European Pat. Off. | 128/203.15 |
| 7525 | of 1907 | United Kingdom | 128/203.21 |
| 2142246 | 1/1985 | United Kingdom | 128/203.21 |

*Primary Examiner*—Kimberly L. Asher
*Attorney, Agent, or Firm*—Robert M. Wolters

[57] ABSTRACT

A powder inhaler and process are provided for aerosolizing finely powdered or pulverized medication and a gas provided in a pillow or blister-type container of extremely thin elastic suitable plastic construction. The pillow is compressed between an anvil with a conical depression and a confronting conical piston. The conical depression has a small orifice at its apex, and the periphery of the pillow is restrained so that compression between the conical pillow and the conical depression produces explosive rupture of the pillow and exit of the gas and medication at a very high speed up to supersonic through said orifice. Medication particle clumps are very efficiently separated into separate particles, and the gas/medication exiting from the orifice are conveyed through a very small area linear or curved tube to a dispersal chamber or directly to a patient, movement through the tube producing a shearing action further enhancing separation of aggregated particles of powder medication.

24 Claims, 2 Drawing Sheets

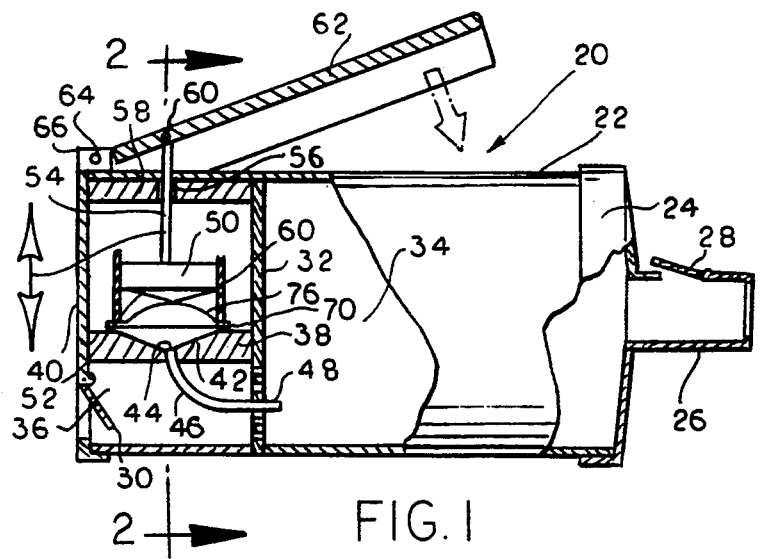
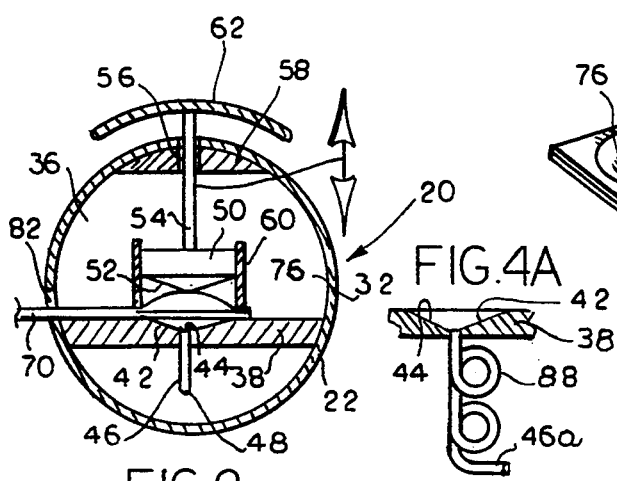
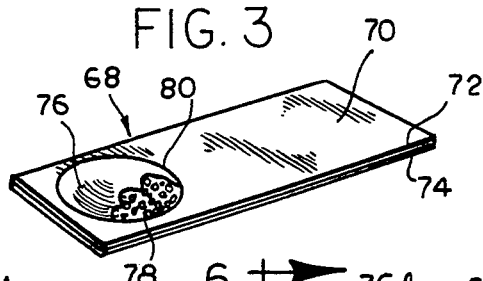
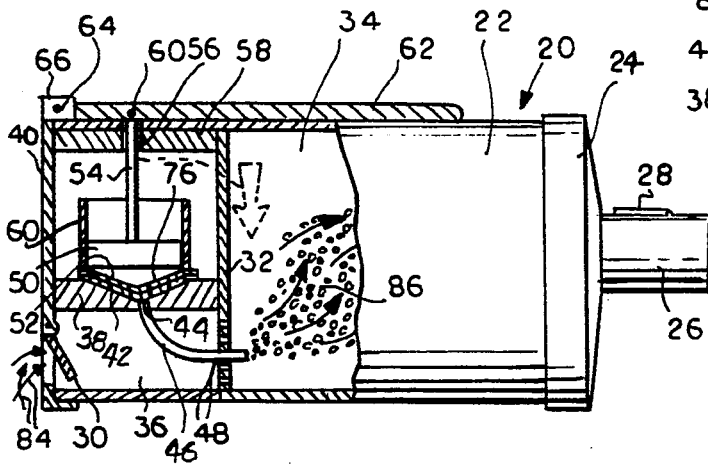
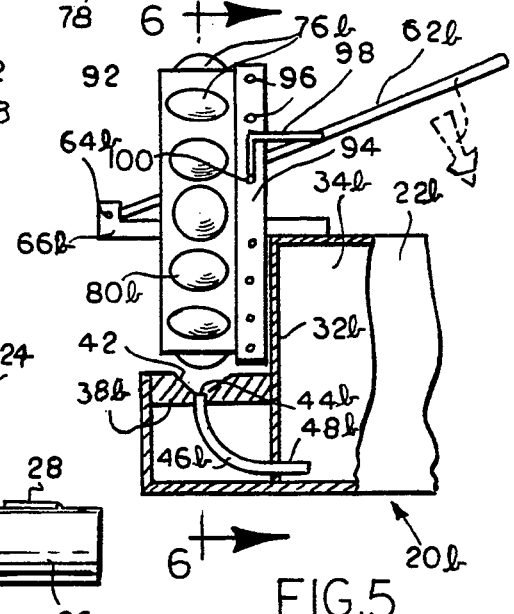

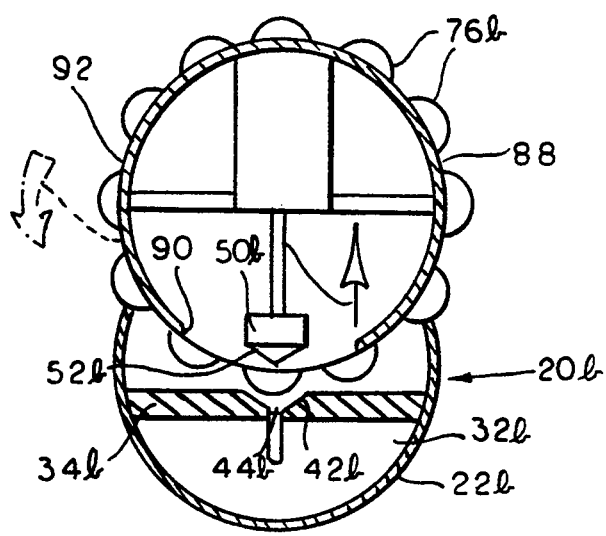
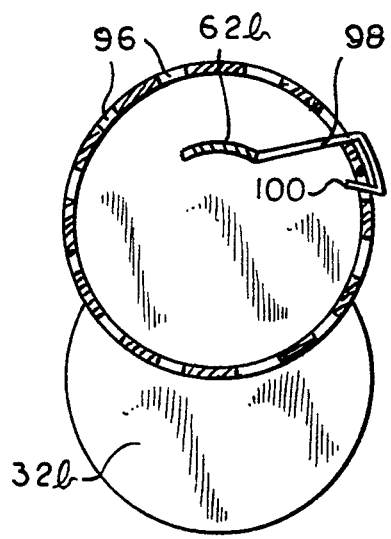
FIG.6  FIG.7
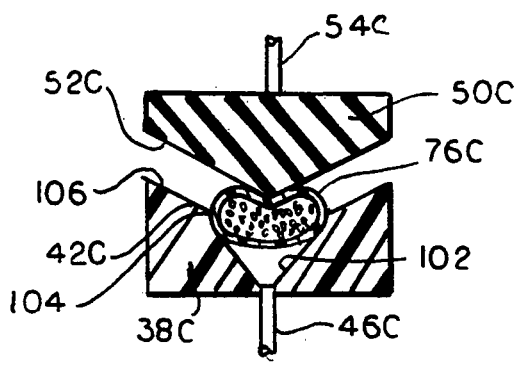
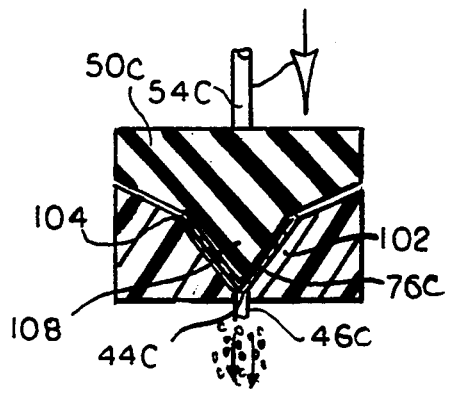
FIG.8  FIG.9
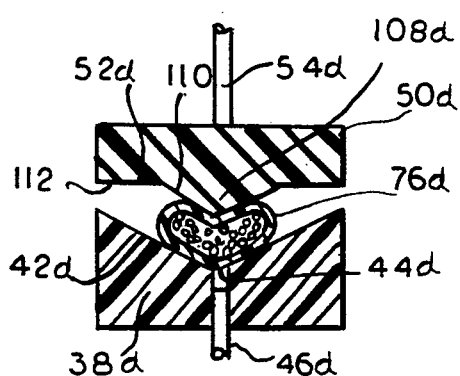
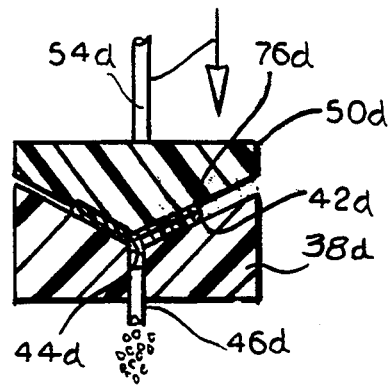
FIG.10  FIG.11
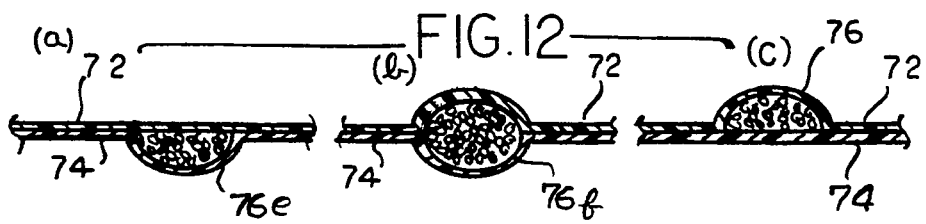
FIG.12

DRY POWDER INHALER AND PROCESS THAT EXPLOSIVELY DISCHARGES A DOSE OF POWDER AND GAS FROM A SOFT PLASTIC PILLOW

BACKGROUND OF THE INVENTION

Patients suffering from asthma or any of many other lung diseases require delivery of medication to the bronchi or to the lungs. At the present time there are three major ways of delivering aerosol treatment or medication to such patients, namely (1) nebulizers, which may be of the (a) venturi-jet type, or of the (b) ultrasonic piezoelectric type which produce aerosols from drug solutions, (2) metered dose inhalers (MDI) consisting of fluorocarbon or other gas pressurized canisters. Dry powder inhalers (DPI) may be (a) Passive or (b) Active. DPI also provide metered doses if sufficient suction is supplied by the patient.

Metered dose inhalers both MDI and DPI are superior to nebulizers because they are readily portable, and do not generally require an external power source such as compressed air or electricity. MDI and DPI are also capable of generating aerosols that are suitable for inhalation, more efficiently, reliably and cost effectively. The pressurized canister type of aerosol generator (MDI) includes a valve, which, when actuated, causes dispersement of a metered quantity of drug.

Because MDIs have previously used a chlorofluorocarbon as the propellant, and chlorofluorocarbons are believed to have a highly adverse effect on the ozone layer surrounding the earth, they are gradually being phased out to be replaced by the environmentally more friendly hydrofluorocarbons (e.g., HFC 134a and 227).

Such metered dose inhalers have become popular in that a droplet aerosol consisting of the drug particles and the fluorocarbon propellant is generated. The fluorocarbon propellant evaporates rapidly, and leaves smaller drug particles and clumps of particles, at least some of which are on the order of 1–3 microns aerodynamic mass median diameter which is the ideal size range for medication aerosols in humans. Unfortunately, many of the particles remain in larger clumps, and do not reach the necessary areas in the bronchi and lungs.

There are some currently available powder inhalation systems which do not require a propellant. However, they do not function very effectively unless the patient can generate flow rates greater than 30–60 liters per minute, since it is the energy provided by the patient's forceful inhalation that not only mobilizes the powder but also breaks up the clumps thus preparing it for inhalation, in contrast with the high pressure of the fluorocarbon or other propellant in metered dose inhalers which accomplish the same end. The patient's inhalation then carries the medication aerosol into the air passages via a mouthpiece whichever aerosol generation method is used. Such current powder inhaler systems require strong inhalation on the part of the patient. They have not worked effectively with patients who cannot inhale vigorously.

In the metered dose inhalers noted above, it is common practice to include surfactants such as oleic acid. This presents problems. The fluorocarbon-medication suspension emerges as a liquid jet from the end of the valve stem or from the end of a cannula attached to the valve stem through which the metered dose inhaler contents have been forced and about 80 percent of it is deposited within three or four centimeters of the end of the valve or cannula. This results in an inefficient delivery system. It further has the disadvantage that large amounts of the surfactant material are deposited on the lining of the trachea, and the first few bronchi. It has been demonstrated that this causes injury to the airway lining with ulceration. Using a pure powder medication should avoid such problems, since it is the excipients in the formulation, rather than the medication that may cause this problem.

Over a period of the last 25 years aerosol therapy has become a mainstay of the treatment of airway diseases, particularly asthma and chronic obstructive pulmonary diseases, such as chronic bronchitis and emphysema as well as bronchiolitis and bronchiectasis (e.g., cystic fibrosis). It is also becoming increasingly important for delivery of antibiotics directly to the airway for chronic illnesses such as cystic fibrosis, for treating a type of pneumonia in immunosuppressed patients (e.g., in AIDS), and for providing a new class of medications (sodium channel blockers) in cystic fibrosis to "lubricate" the secretions and make them easier to cough up or remove as a result of the action of cilia. Other aerosol medications include mucolytic agents to thin secretions, the newest of which is deoxyribonuclease made by a recombinant method (rhDN-ase). Within about the last year exciting developments have occurred with regard to the delivery of several important peptide hormones by the aerosol route, because they would otherwise be inactivated by stomach acid if they were ingested. Most recently, there has been very interesting work from the National Institutes of Health (Dr. R. Crystal), showing that genes can be inserted into inactivated common cold viruses, and delivered by the aerosol route to mice with a missing gene which can, in this way, be replaced. Even more recently, the New York Times reported that the first experiments in humans were now being undertaken using the same methods to attempt to correct the genetic defect of cystic fibrosis, thus actually curing the disease. Thus the future for an ever increasing role for aerosols in pulmonary and even systemic disease therapy looks very promising.

Aerosol delivery systems generally fall into one of two categories, either (1) active or (2) passive. (1)"Active" devices include (a) metered dose inhaler (MDI) and (b) wet nebulizers. The pressurized canister metered dose inhaler (a) MDI [which] generates the aerosol and directs it towards the patient independently of the patient's force of inhalation. This provides aerosol to the patient in a manner similar to so called "wet nebulizers" that aerosolize a drug solution (jet nebulizers using the venturi principle, the energy source being compressed air which also serves to direct aerosol towards the spontaneously breathing or ventilation assisted patient, and ultrasonic nebulizers utilizing high speed vibration of a piezo-electric crystal and a blower fan to carry the medication aerosol to the patient). These are all active aerosol devices, since with the jet nebulizer it is the flow of oxygen or air through the device that creates the aerosol and drives it towards the patient who can then breathe in from a mouthpiece or mask, while with the ultrasonic nebulizer the aerosol is generated into a space from which it can be inhaled by the patient breathing normally to inhale the mist with each normal inhalation, even if that inhalation is not vigorous. Furthermore, a blower can be incorporated which pushes the aerosol from the ultrasonic generator toward a mask or mouthpiece from which the patient inhales.

In contrast, currently available powder inhalers are "passive" devices in that the drug powder must reside in a small reservoir from which the patient can suck it by creating a relatively high inspiratory flow rate, usually over 30 L/min (liters per minute), and sometimes as high as 90-120 L/min if the optimum dose of medication is to be provided. This type of device has the advantage that aerosol is inhaled automatically when the patient inhales vigorously, but has the disadvantages that (a) there is considerable variability in dose depending upon how vigorously the patient inhales, (b) during severe episodes of asthma it may not be possible to create the high flow rates necessary to get a full dose of the drug (this is particularly true of children under the age of 6), and (c) the greatest efficiency for aerosol inhalation is achieved at low inspiratory flow rates, 45 L/min and below, because at high flow rates small particles have greater inertia and therefore fore act like larger particles, thereby tending to be deposited in the back of the throat and around the larynx by impaction rather than being carried into the airways of the lungs where the medication must be deposited to be effective. Another disadvantage of some widely prescribed current powder systems relates to exposure to the humidity of the environment of the drug reservoir where the fine particles are stored. Since many drug particles are very hygroscopic, repeated or continual exposure to humidity will greatly reduce the available dose due to swelling and clumping.

In recent years there has been increasing emphasis on powder inhaler systems, because they do not require pressurizing chemicals and because they provide medication on inhalation without having to devote as much time in teaching patients to coordinate aerosol discharge with inhalation (as is the case with MDI devices). The newest of these, known as a Turbuhaler, contains pure drug powder rather than drug powder mixed with lactose that is required in some of the other devices. Lactose is used to disperse the powder in most older devices. It is not a big issue, but because the particles are rather large they often cause patients to cough, whereas pure drug powders are much less likely to do so. Current powder inhaler systems are incapable of being used in patients who are breathing quietly such as infants and young children, and are of no use in ventilator circuits or with relatively uncooperative patients, nor can they be directed down thin cannulas in intubated patients.

Active systems (MDI and nebulizers) are extremely useful in the settings noted above, and indeed can be used in treating virtually all patients if appropriate adapters to the MDI canister, or to the nebulizer are used. Because MDI based systems, using appropriate accessory attachments are much more versatile, efficient, portable and cost effective, they are rapidly replacing wet nebulizers if appropriate MDI drug formulations are available. From the foregoing, it should be evident that active aerosol systems are inherently superior to passive systems, and that an active powder inhaler system would probably become the aerosol generation system of choice, and probably would supersede both current pressurized metered dose inhalers and passive powder systems currently available. If such a powder system could be made to approach the versatility of currently available fluorocarbon driven metered dose inhalers, it would likely make obsolete most other aerosol delivery systems, including nebulizer systems. It is probable that active powder systems could employ pure drug powder, and if provided with appropriate attachments, such as a valved mouthpiece or fine cannula extensions or with a mask to allow their use in infants, children and adults breathing normally, or even in asthmatic animals such as horses or cattle, as are presently available for use with metered dose inhalers, these would serve a wide variety of clinical needs in a variety of patients of all ages.

There are significant limitations of current MDIs in that metered dose inhalers are relatively inefficient because they produce mainly non-respirable particles. Another important issue with pressurized canister inhalers relates to the output of particles that range in size from about 35 $\mu$m (micro meter) to about 1 $\mu$m. Of this so called heterodisperse aerosol only about 30 percent (chiefly particles under 5 $\mu$m) is actually capable of being inhaled. In practice this figure is closer to 20 percent. Most of the rest of the aerosol which is deposited in the throat has the potential for causing side effects, while not contributing to the therapeutic benefit.

We set forth the following characteristics as being those of an ideal aerosol system, which ideal aerosol delivery system would:

1. Be an active system with a reproducible dose output;
2. Completely dispense with pressurizing chemicals and excipients (additives in the formulation that enable the system to produce aerosol, but do not contribute to therapy);
3. Contain only pure drug;
4. Create smaller and more uniform particles almost exclusively (smaller than 5 $\mu$m), thus improving the efficiency of drug delivery to the airways of the lungs;
5. Dispense doses accurately over a wide range, such as 10-1000 ug;
6. Be as foolproof as possible for the patient to use;
7. Be small and easily portable;
8. Contain multiple doses sufficient for at least about a month of therapy; and
9. Be used with a variety of adapters making the system useful in neonatology, pediatrics and adult medicine or even for veterinary medicine for treating chronic illness, acute flareups, and, if necessary, patients who are intubated, and require assisted ventilation because of inability to breathe sufficiently to provide oxygen to their bodies and remove carbon dioxide.

The result of providing almost exclusively very fine and thus "respirable" particles would be that much smaller doses would be required because the system could be much more efficient, with greatly decreased losses of medication in the throat and hopefully reduced cost. We call this approach to aerosol therapy "airway drug targeting", because the inhaled medication largely bypasses the upper airways above the larynx to be deposited fairly uniformly in the airways of the lungs below the larynx.

It is well recognized that powders in storage tend to clump together so that large amounts of energy are needed to create an aerosol cloud of an appropriate size for inhalation.

OBJECTS AND SUMMARY OF THE PRESENT INVENTION

It is an object of the present invention to provide a powder inhaler which generates an extremely fine powdered medication aerosol, very close to the size of the milled individual particles.

Specifically, it is an object of the present invention to provide explosive expulsion of air and medication powder from a plastic "pillow" or "blister" of air and medication.

It is a further object of the present invention to provide a dry powder inhaler in which the explosively expelled drug powder is directed through a straight or a curved cannula to provide shearing of the remaining particle clumps.

In attaining the foregoing and other objects, we propose to provide a pillow-type dry powder inhaler in which a plastic medication blister or pillow contains only powdered medication plus air, nitrogen or other suitable filling gas that is environmentally friendly, yet does not interact with or cause degradation or alteration of the medication. For example, air, carbon dioxide or nitrogen are environmentally friendly. Pressure is applied to such blister or pillow while the structure of the inhaler is such that the blister can rupture explosively in only one direction. The resultant explosion of the medication blister produces a shockwave, and the air and medication are ejected at high speeds up to twice the speed of sound. This produces a popping noise that is equivalent to the bang that a balloon makes when it explodes. As a result, an ultrafine aerosol is produced, very close to the size of the milled individual particles. This ultrafine aerosol further is directed toward the patient by means of a rather small structure that incorporates a thin straight or curved cannula which shears any remaining particle clumps as they are driven toward the mouthpiece.

This provides a simple device that allows complete dissociation of aerosol generation and inhalation, since the majority of ultrafine inhalable particles stay suspended in the dispersal chamber (which is actually also mouthpiece) for 5–10 seconds. It is known that a particle of 3 μm settles in still air at a rate of about 3/10 cm per second, whereas a particle 1 μm has a settling velocity about 10 times longer, namely 3/100 cm per second. This may completely eliminate the need for any kind of mechanical system that current active aerosol generators of the MDI type required to assure aerosol delivery on inhalation. The device includes a one-way valve as known in the art so that patients are prevented from exhaling into and disbursing the aerosol before it could be inhaled. Inspiratory and expiratory valves are incorporated which allows the aerosol to be inhaled during ordinary quiet breathing by uncooperative adults, infants and small children to whom the medication could be administered by means of a mask held over the face by a caregiver such as a nurse or a parent.

To protect the drug powder from humidity, packaging in individual blisters is superior to drug hoppers or reservoirs. A device in current clinical use provides drug blisters in the form of a multiple disc, and prior art also proposes a 60 dose blister strip.

We are aware of one reference which superficially has some commonality with our invention. European Patent Publication 0 469 814 A1 discloses an inhaler utilizing blister packaging of medication. However, the blister is partly plastic film, and partly metallic film. The metallic film may be scored to facilitate rupturing thereof. Pressure is applied which causes the metallic film to rupture relatively slowly due to separation of the metallic film substantially anywhere within the area of the blister. The powder is thereby released and simply dumped into a chamber from which the medication is inhaled by a patient. There is no explosive rupturing of a blister under the tension from the pressure of compressed air or other gas, and it is apparent that considerable clumping of the dumped medication is expected as structure, apparently a filter, is provided at 48 which is said to resist or diminish aggregation of the powder particles, apparently simply by removing large particles. This obviously produces a highly inefficient delivery of medication to the patient, and would result in trapping relatively large amounts of powder in the throats of patients.

THE DRAWINGS

Our invention will be readily understood from reading the following specifications in connection with the accompanying drawings wherein:

FIG. 1 is a side view, partially in section, illustrating an inhaler constructed in accordance with the principles of the present invention;

FIG. 2 is a cross sectional view substantially along the line 2—2 in FIG. 1;

FIG. 3 is a perspective view of a plastic tab including a single blister of gas and medication;

FIG. 4 is a side view partially in axial section corresponding to FIG. 1 and showing dispersal of the medication;

FIG. 4*a* is a fragmentary view showing a modification of the cannula exiting from the pressurized area;

FIG. 5 is a fragmentary view similar to a portion of FIG. 1, showing a modification incorporating a plurality of blisters on a belt for multiple dosage;

FIG. 6 is a cross sectional view taken substantially along the line 6—6 in FIG. 5;

FIG. 7 is a view axially displaced from FIG. 6 showing mechanism for effecting movement of the plurality of blisters;

FIG. 8 is a fragmentary sectional view showing a practical form of the pressuring and explosion producing device prior to explosive rupturing of a blister;

FIG. 9 is a view similar to FIG. 8 showing the position of the parts at the moment of explosive rupturing;

FIG. 10 is a view similar to FIG. 8 and showing a modification of the invention;

FIG. 11 is a view showing the parts of FIG. 10 in a later position, thereby being equivalent to FIG. 9; and FIG. 12 shows three different blister cross sections, respectively at (a), (b), and (c).

DETAILED DESCRIPTION OF THE ILLUSTRATED EMBODIMENTS

A pillow type dry powder inhaler 20 constructed in accordance with and illustrating the principles of the present invention is shown in FIGS. 1-4. This inhaler is a compact hand-held unit, and is fabricated of suitable plastic (resinous plastic) material. It includes a hollow cylinder 22 providing a dispersal chamber which holds the dispersed powder in the air until it is inhaled. This cylinder includes a one-way valve 28 to prevent the patient from exhaling into the chamber when the dispersed powder is in the chamber. A cap 24 secured at the outlet end of the chamber 22 is provided with a mouthpiece 26 through which air and powder exit into the patient's mouth. The exhalation valve 28 is provided on the mouthpiece, and is normally closed. This may be through an integral plastic hinge normally holding the flap of the valve closed, or it may be a conventional hinge with a spring incorporated. As will be understood, if the patient exhales the valve 28 will open. In addition, there is an inhalation valve 30 which is normally biased closed. When a patient inhales air is drawn into the chamber 22 so that the dispersed powdered medication may be inhaled by the patient.

A transverse partition wall 32 isolates the left end of the cylinder 22, thereby defining the dispersal chamber 34 and the medication entering end or chamber 36 of the cylinder 22.

A horizontal wall 38 extending from the partition wall 32 to an end cap 40 is of greater thickness as it serves as an anvil for rupturing the blister or pillow to be described shortly hereinafter. The wall 38 preferably extends from the cylindrical surface on one side to the cylindrical surface on the other side. The wall or anvil 38 is provided centrally with a conical or funnel-shaped depression 42, opening at the apex 44 thereof into a tube 46 of straight or curved nature and of varying length and (small) diameter which opens through the wall 32 at 48 in order to discharge powdered medication and air or other gas from the blister into the chamber 34. The inhalation valve 30 is in the vertical wall of the end cap 40 below the wall 38. The wall 32 is perforated below the wall 38 to pass air from the valve 30.

Spaced above the wall 38 there is a piston 50, the upper portion of which is cylindrical, having a lower surface 52 of conical nature. As is seen best in FIG. 4 the conical surface 52 is complimentary to conical or funnel-shaped depression 42. A piston rod 54 extends axially upwardly from the piston 50 through an opening 56 in a reinforcing member 58 secured to the interior of the cylinder 22. The opening 56 also extends through the cylinder. The piston rod is pivotally connected at its upper end at 60 to a manually operable lever 62. This lever 62 is arcuate in nature so as to conform to the exterior of the cylinder 22. The lever is pivoted at its left end as seen in the drawings at 64 to an upright member 66 at the upper left portion of the cylinder 22, and specifically on the end cap 40. The lever 62 is normally biased diagonally upwardly as shown in FIG. 1, and is manually closable upon gripping of the lever against the cylinder 22 as shown in FIG. 4. It will be understood that instead of the pivot connection at 60 there could simply be a sliding connection against the underface of the lever.

A cylinder 60 surrounds the piston 50, and more about this will be set forth substantially immediately hereinafter.

Before proceeding further with the dry powder inhaler 20 it will be profitable to consider a blister package 68 of medication as shown in FIG. 3. The package 68 comprises a tab 70 which consists of two layers of plastic material, an upper layer 72 and a lower layer 74. Both layers or sheets are made of a plastic material such as polyethylene or other suitable material. Each layer or sheet 72, 74 is about 0.02 mm thick. One or both of the layers or sheets is outwardly deformed to provide a blister or pillow 76 containing medication and dry air, nitrogen or other suitable gas. The air or gas is substantially at atmospheric pressure. Any gas can be used, but nitrogen is inexpensive and has superior preservation powers insofar as the powdered medication 78 is concerned. The blister has a circular periphery 80, and may bulge outwardly in a more or less spherical pattern. Except for the area within the circle 80 of the blister 76 the plastic sheets 72 and 74 are adhered together by known techniques, such as sonic welding, adhesives, etc.

Returning now to consideration of the powder inhaler 20, there is provided an opening or slot 82 (FIG. 2) immediately above the wall 38. The patient or a caregiver may grip the tab 70 of the medication package between thumb and forefinger, and insert it through the opening 82 to position the blister 76 in axial alignment with the piston 50 and conical or funnel-shaped depression 42. As will be readily understood, the cylinder 60 must be lifted somewhat during such insertion to permit positioning of the blister 76. The cylinder is subsequently lowered so that the bottom edge thereof presses against the tab closely about the circle 80 to provide radial containment of the blister. Specific details for raising and lowering the cylinder 60 are not shown, but will be readily understood by anyone skilled in the mechanical arts. For example, there could be a connection between the cylinder 60 and the lever 62, preferably including a compression spring. The cylinder would be raised whenever the lever is raised to the position shown in FIG. 1, and would be pressed down tightly against the tab 70 closely encircling the periphery 80 of the blister 76. The blister is thus contained on all sides by the piston 50, depression 42, and cylinder 60. Pressure builds up on the blister and eventually the blister ruptures explosively through the apex 44 of the conical depression 42. There simply is no where else that it can break in view of its complete containment as noted just above. When the blister breaks it does so with an audible pop, and the air/medication powder exits the blister at a high speed of up to twice the speed of sound, i.e., mach 2. This explosive exiting of the air/powder from the blister effects a remarkably efficient separation of the particles of medication by shattering apart the aggregate clumps of drug powder. The air/powder must pass through the curved tube 46 to the chamber 34. Portions of the air/powder mix must travel more rapidly along the outer portion of the bend than along the inner portion thereof. This causes a shearing action which further enhances separation of the individual particles of the medication. As the air/powder mix exits the tube 46 into the chamber 34 it expands very rapidly and mixes with the incoming air 84 through the valve 30 to expand with a tumbling, shearing action as indicated at 86. The medication then is inhaled through the mouthpiece 26 by the patient upon simple inhalation breathing through the mouth or through the nose for nasal aerosol treatment, without the necessity of any great effort or timing on the part of the patient or even while breathing in and out normally.

The force required to rupture the pillow is about 45 N, and the force required on the handle is only about 11 N or less, in view of the lever action. Thus a cocked spring held by a detent attached to a valve flap could easily automate aerosol discharge on inhalation.

Several advantages are obtained by the foregoing. Dry powder is sealed in the pillow or blister when fabricated in a factory so that dry powder is released into the chamber even after months or years of storage. No desiccant is needed in the powder or elsewhere in the inhaler. The powder is efficiently dispersed by shearing action in the high velocity flow exiting the conical depression 42 and passing through the narrow curved tubing 46. No dispersant need be added to the powder. The powder is metered in the manufacturing where it can be done with great accuracy. Only a small percentage of the powder remains in the pillow after discharge. As noted, a popping noise is produced when the pillow ruptured. This generally will be sufficient to assure the patient that a dose has been administered. However, it may desirable to add a minute amount of an artificial sweetener to the powder. The taste would enhance the assurance that the dose has been given. The inhaler unit can be used for thousands of doses if medication blister cartridge replacements are provided. As noted heretofore, nitrogen or some other inert gas can be used to fill the pillow or blister during manufacture. This inhibits oxidation of the drug. The inhaler can be used for many types of drug and levels of dosage. Such information can be applied to the blister cartridge or the tab individual blister by color or pattern coating such as bar coding.

A modification of the structure heretofore described is shown in FIG. 4*a*. Most of the parts are identical with those heretofore shown and described, and either are not specifically shown, or are identified by the same numbers. The change resides in a modification of the tubing 46*a*. The tubing instead of being a single curve includes a spiral of one or more turns. This enhances the shearing action, thereby further ensuring substantially complete separations of the particles of medication, with improved aerosolization if needed.

The invention is adapted for multiple dose usage. The tab cold be extended to a long strip bearing many blisters of medication and coiled into a spiral strip. Discs of medication are known. A modification of the invention is shown in FIG. 5–7 in which a plurality of blisters is provided in a single belt carrier. This is of value to patients who must rather frequently inhale medication. Similar numerals are utilized to identify corresponding parts with the addition of the suffix b. Differences in structure are insufficient to require description thereof, except as noted hereinafter. A generally cylindrical carrier 88 has a downwardly opening gap 90 for carrying a continuously ring belt 92 slidable thereon. The inner diameter of the belt is just enough more than the outer diameter of the carrier 88 to permit easy installation axially onto the carrier, and to permit rotary motion of the belt on the carrier. The belt is provided with a plurality of blisters 76*b* extending radially outwardly. This portion of the belt is a double layer portion like the tab 70 previously described. A sheet of plastic comprising the belt is about 0.02 mm thick. In addition, there is a narrow plastic belt 94 secured to one edge of the previously mentioned plastic belt and provided with arcuately spaced perforated holes 96. The pillow carrying belt 92 is about 1 cm wide, and would hold 12 medication doses in a belt 4 cm in diameter. The belt 94 is about 2 mm wide and 0.1 mm thick.

A right angle spring arm 98 is secured rigidly to the operating lever 62*b* and has a hook 100 on its end 20. When the lever 62*b* is raised (a spring may be provided for automatic raising) the spring hook 100 catches in one of the holes 96 and advances the belt rotationally a distance equal to the spacing between blisters. When the lever is depressed the hook 100 is raised from the hole and slides along the narrow belt 94 to catch the next hole for again advancing the belt when the lever is next raised. The inhaler is stored with the lever depressed, by means such as an encircling anchor band (not shown) until the next dose is needed. Alternatively, the spring pivot 64*b* can hold the lever depressed, and it can then be raised manually for use.

Two practical forms of a piston and anvil are shown in FIGS. 8–11. The piston in the usual case is made of a rubber compound, as is the anvil, the later being quite rigid. In FIGS. 8 and 9, similar numerals again being used, this time with the addition of the suffix c. In this embodiment of the invention the piston 50*c* is made of a relatively soft, deformable rubber material. The conical active surface 52*c* is of the same shape as previously discussed. However, the conical depression 42*c* in the anvil 38*c* is somewhat different. The central conical portion 102 is of a substantially steeper angle than the conical angle 52*c* of the piston. The central, steep portion of the cone joins at an annular ring 104 with a shallower conical section 106 of the same angle as the conical surface 52*c* of the piston. The parting ring 102 is of substantially the same diameter as the diameter of a pillow or blister 76*c*.

In FIG. 8 the piston has just engaged the blister and is starting to deform it. The radially outer portion of the piston surface 52*c* engages the complementary surface 106 of the anvil. Before too much pressure is applied to the blister the surface 52*c* engages the surface 106 thereby to provide peripheral restraint of the blister. As further lowering of the piston occurs (see FIG. 9) the central portion of the piston deforms departing ring 104 inwardly to a sharper conical shape conforming to the shape 102 of the depression 42*c*. Thus, as shown in FIG. 9 the blister 76*c* is compressed to the point where it explosively bursts through the orifice 44*c*. The air/-medication powder mix again exits into the tube 46*c* at very high speed up to mach 2, and continues on into the dispersal chamber as before. That is to be borne in mind that the plate or anvil 38*c* is quite hard and rigid, while the piston 50*c* is relatively soft and pliable, to effect the action just described.

Modification of the foregoing is shown in FIGS. 10 and 11. In this instance, the anvil or depression is again hard and rigid. In this instance the conical depression is of a constant angle. The piston 50*d* has a central portion 108*d* of the same angle as the angle of the conical depression 42*d*. However, outwardly of a parting ring position 110 the undersurface 112 of the piston is flat. As the piston moves from the starting position of FIG. 8 to the final position of FIG. 9, the outer flat ring 112 engages the conical surface 42*d*, and compresses and deflects to a surface conforming to the conical surface 42*d*, thereby providing peripheral restraint of the blister 56*d*. Again, the blister can rupture only through the orifice 44*d*, and again ruptures explosively to expel the air/medication powder mix at supersonic speed.

The blister is capable of being formed in different shapes. This is illustrated in FIG. 12. In FIG. 12(*a*) the top plastic strip or layer 72 is flat, and the blister 76*e* extends downwardly as a part of the layer 74.

In FIG. 12(*b*) the blister 76*f* extends both upwardly from the upper plastic sheet 72 and downwardly from the lower plastic sheet 74.

In FIG. 12(*c*) the blister 76 extends upwardly from the upper plastic sheet 72, the lower plastic sheet 74 being flat, as previously discussed throughout this specification.

It will now be apparent that we have provided an inhaler in which dry powder contained in a plastic pillow or blister is restrained in all directions, except through the downwardly opening orifice into the curved tube 46. As pressure is applied, the air within the blister is to some extent compressed, but ultimately the pressure within the blister becomes sufficient that the blister ruptures explosively through the small orifice into the tube at up to supersonic speed, thereby breaking up the powder clumps into the individual particles. Movement through the curved tube produces a shearing action which further separates the particles, and as they exit at supersonic speed into the dispersal chamber mouthpiece from which the medication is inhaled the particles are separated very efficiently.

The member 26 has been specifically disclosed as a mouthpiece. However, it will be noted that the "mouthpiece" is of rather small cylindrical shape, and could easily be connected directly to a mask, to a tube leading to a mask, or to an endotracheal tube.

The dispersal chamber is of value primarily in holding the suspended medication particles until the patient inhales, since complete particle separation is effected by the very high speed, explosive ejection of the powder from the blister, enhanced by the shearing action of the powder passing through the tube 46. This tube produces a shearing action even if straight since air (gas) velocity near the center will be greater than near the wall of the tube. The dispersal chamber could be dispensed with, and the tube 26 could exit directly into the "mouthpiece" or into the patient's nose, mouth or windpipe preferably tuned with the patient's inhalation. In such circumstance, the tube could vary quite substantially in size. As a further variation, the mouthpiece could be replaced by a nasal adapter. Medication particles could be sprayed directly into the nose, or sniffed up from the expansion chamber.

The specific examples of the invention as herein shown as described are for illustrative purposes only. Changes will possibly occur to those skilled in the art, and will be understood as forming a part of the present invention insofar as they fall within the scope of the appended claims.

The invention is claimed as follows:

1. A powder inhaler assembly for dispersing medication, said assembly not using a propellant, said assembly comprising a pillow containing a dose of powdered medication and gas, said pillow constructed of plastic means for explosively discharging the powdered medication and gas from inside said pillow comprising a housing having a dispersal chamber, means providing an exit from said chamber for transporting dispersed medication to a patient, a support in said housing, said support having a depression of predetermined shape and having a maximum transverse dimension of predetermined size, said depression having an outlet orifice which is small relative to said predetermined size, a piston positioned opposite to said depression and having a surface confronting said depression which at least in part conforms to said depression, means for moving said piston towards said depression to compress a medication pillow therein, means associated with said piston and said depression for providing peripheral support to a medication pillow, said pillow being completely restrained except for said orifice, the gas in said pillow compressing responsive to continued movement of said piston toward said depression and resulting in explosive rupturing of said pillow, said dose and gas exploding and deaggregating into said orifice and through said orifice, for inhalation by a patient, wherein said exit means includes a conduit means from said orifice to said dispersal chamber for transmission of aerosolized medication to a patient.

2. A powder inhaler assembly as set forth in claim 1 wherein said depression is at least in part conical, said conical depression having an apex, said outlet orifice being located at said apex.

3. A powder inhaler assembly as set forth in claim 2 wherein said peripheral restraint comprises a cylinder.

4. A powder inhaler assembly as set forth in claim 1 wherein said peripheral restraint comprises a cylinder.

5. A powder inhaler assembly as set forth in claim 1 wherein said peripheral support comprises conformation of one of said depression and said piston which is initially nonconforming to the other such that radially outward portions of said piston and said depression engage before radially inner portions, at least one of said piston and said depression subsequently deforming to conform to the shape of the other thereof.

6. A powder inhaler assembly as set forth in claim 5 wherein said depression is conical having an apex, said orifice being disposed at said apex.

7. A powder inhaler assembly as set forth in claim 6 wherein the radially outer portion of said depression has a predetermined angle, and a radially inner portion thereof has a steeper angle, said piston being constructed of deformable material, and a radially inner portion of said piston deforms to conform to said radially inner portion of said depression.

8. A powder inhaler assembly as set forth in claim 6 wherein said conical depression has a predetermined angle, said piston has a radially inner portion conforming to said conical depression and having the same predetermined angle, a radially outer portion of said piston having a different angle, said piston being deformable to conform to said conical depression.

9. A powder inhaler assembly as set forth in claim 8 wherein the radially outer portion of said piston is flat.

10. A powder inhaler assembly as set forth in claim 9 wherein said conduit means has a small cross section relative to said predetermined size to provide shearing forces enhancing deagregation of said powdered medication.

11. A powder inhaler assembly as set forth in claim 10 wherein said conduit means is curved.

12. A powder inhaler assembly as set forth in claim 10 wherein said conduit means comprises a spiral.

13. Apparatus for dispersing of medication, said apparatus not using a propellant, said apparatus comprising, a pillow containing powdered medication and a gas together in said pillow said pillow being of plastic construction; said apparatus further comprising means for explosively discharging the powdered medication and gas from within said pillow comprising a base, a support on said base, said support having a depression of predetermined shape and having a maximum transverse dimension of predetermined size, said depression having an outlet orifice which is small relative to said predetermined size, a piston positioned opposite to said depression and having a surface confronting said depression which at least in part conforms to said depression, means for moving said piston towards said depression to compress said medication pillow positioned therein, means associated with said piston and depression for providing peripheral support to said medication pillow, said pillow being completely restrained except for said orifice, the gas in said pillow compressing responsive to continued movement of said piston toward said depression and resulting in explosive rupturing of said pillow, said dose of powdered medication and gas exploding and deaggregating into said orifice for inhalation by a patient.

14. Apparatus as set forth in claim 13 and further including a conduit of small cross section relative to said predetermined size leading from said orifice for enhancing of deaggregation by shearing action.

15. Apparatus as set forth in claim 14 wherein said peripheral restraint comprises a cylinder.

16. Apparatus as set forth in claim 13 wherein said peripheral restraint comprises a cylinder.

17. Apparatus as set forth in claim 13 wherein said peripheral support comprises conformation of one of said depression and said piston which is initially non-conforming to the other such that radially outward portions of said piston and said depression engage before radially inner portions, at least one of said piston and said depression subsequently deforming to conform to the shape of the other thereof.

18. Apparatus as set forth in claim 17 wherein said depression is conical having an apex, said orifice being disposed at said apex.

19. Apparatus as set forth in claim 18 wherein the radially outer portion of said depression has a predetermined angle, and a radially inner portion thereof has a steeper angle, said piston being constructed of deformable material, and a radially inner portion of said piston deforms to conform to said radially inner portion of said depression.

20. Apparatus as set forth in claim 18 wherein said conical depression has a predetermined angle, said piston has a radially inner portion conforming to said conical depression and having the same predetermined angle, a radially outer portion of said piston having a different angle, said piston being deformable to conform to said conical depression.

21. Apparatus as set forth in claim 20 wherein the radially outer portion of said piston is flat.

22. A process for propellant free dispersing of powder medication, said process comprising the steps of providing a plastic pillow containing powder medication and a gas, completely surrounding said pillow except for a very small area relative to the size of said pillow, explosively rupturing said pillow at said small area by compressing said pillow and the gas within said pillow while so surrounded and thereby deaggregating said powder medication, and delivering said deaggregated powder medication to a patient for inhalation.

23. The process as set forth in claim 22 and further including the step of guiding gas and medication from said very small area along a path of small cross section to produce a shearing action further separating clumps of medication.

24. The process as set forth in claim 23 wherein the step of guiding gas and medication along a path of small cross section comprises moving said powder medication and gas along a curved path.

* * * * *